(12) United States Patent
Foley et al.

(10) Patent No.: US 8,500,813 B2
(45) Date of Patent: *Aug. 6, 2013

(54) MINIMALLY INVASIVE SPINAL DISTRACTION DEVICES AND METHODS

(75) Inventors: Kevin T. Foley, Germantown, TN (US); Roy Lim, Germantown, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 56 days.

This patent is subject to a terminal disclaimer.

(21) Appl. No.: 13/117,709

(22) Filed: May 27, 2011

(65) Prior Publication Data

US 2011/0295373 A1    Dec. 1, 2011

Related U.S. Application Data

(63) Continuation of application No. 11/645,825, filed on Dec. 26, 2006, now Pat. No. 7,972,382.

(51) Int. Cl.
*A61F 2/44* (2006.01)

(52) U.S. Cl.
USPC ............ 623/17.12; 623/17.15; 606/105

(58) Field of Classification Search
USPC ............ 606/246–279; 623/17.11–17.16
See application file for complete search history.

(56) References Cited

U.S. PATENT DOCUMENTS

| | | |
|---|---|---|
| 3,875,595 A | 4/1975 | Froning |
| 4,772,287 A | 9/1988 | Ray et al. |
| 4,863,477 A | 9/1989 | Monson |
| 4,932,969 A | 6/1990 | Frey et al. |
| 4,969,888 A | 11/1990 | Scholten et al. |
| 5,002,576 A | 3/1991 | Fuhrmann et al. |
| 5,059,193 A | 10/1991 | Kuslich |
| 5,108,404 A | 4/1992 | Scholten et al. |
| 5,123,926 A | 6/1992 | Pisharodi |
| 5,171,278 A | 12/1992 | Pisharodi |
| 5,236,460 A | 8/1993 | Barber |
| 5,390,683 A | 2/1995 | Pisharodi |
| 5,423,850 A | 6/1995 | Berger |
| 5,480,400 A | 1/1996 | Berger |
| 5,549,679 A | 8/1996 | Kuslich |
| 5,645,597 A | 7/1997 | Krapiva |
| 5,702,450 A | 12/1997 | Bisserie |
| 5,785,647 A | 7/1998 | Tompkins et al. |
| 5,827,289 A | 10/1998 | Reiley et al. |
| 5,928,284 A | 7/1999 | Mehdizadeh |
| 5,972,015 A | 10/1999 | Scribner et al. |
| 6,039,761 A | 3/2000 | Li et al. |
| 6,126,689 A * | 10/2000 | Brett .................. 623/17.16 |
| 6,127,597 A | 10/2000 | Beyar et al. |
| 6,159,215 A | 12/2000 | Urbahns et al. |
| 6,174,334 B1 | 1/2001 | Suddaby |

(Continued)

FOREIGN PATENT DOCUMENTS

| | | |
|---|---|---|
| EP | 0 260 044 A1 | 3/1988 |
| WO | WO 00/35389 | 6/2000 |
| WO | WO 00/44319 | 8/2000 |
| WO | WO 01/19295 | 3/2001 |

*Primary Examiner* — Andrew Yang

(57) ABSTRACT

Systems are provided for reducing the complexity and invasiveness of spinal stabilization procedures and provide an expandable device deliverable to a spinal implantation location. The expandable device can be delivered through a minimally invasive access portal and expanded at the implantation location to manipulate one or more bony structures or maintain a configuration of one or more bony structures.

14 Claims, 9 Drawing Sheets

U.S. PATENT DOCUMENTS

| | | |
|---|---|---|
| 6,183,517 B1 | 2/2001 | Suddaby |
| 6,190,414 B1 | 2/2001 | Young et al. |
| 6,248,110 B1 | 6/2001 | Reiley et al. |
| 6,280,456 B1 | 8/2001 | Scribner et al. |
| 6,332,894 B1 | 12/2001 | Stalcup et al. |
| 6,402,785 B1 | 6/2002 | Zdeblick et al. |
| 6,409,766 B1 | 6/2002 | Brett |
| 6,419,704 B1 | 7/2002 | Ferree |
| 6,419,705 B1 | 7/2002 | Erickson |
| 6,423,083 B2 | 7/2002 | Reiley et al. |
| 6,436,140 B1 | 8/2002 | Liu et al. |
| 6,440,138 B1 | 8/2002 | Reiley et al. |
| 6,443,989 B1 | 9/2002 | Jackson |
| 6,454,807 B1 | 9/2002 | Jackson |
| 6,491,724 B1 | 12/2002 | Ferree |
| 6,527,799 B2 | 3/2003 | Shanley |
| 6,582,467 B1 | 6/2003 | Teitelbaum et al. |
| 6,676,665 B2 | 1/2004 | Foley et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 2002/0026197 A1 | 2/2002 | Foley et al. |
| 2002/0058947 A1 | 5/2002 | Hochschuler et al. |
| 2002/0183761 A1 | 12/2002 | Johnson et al. |
| 2003/0045939 A1* | 3/2003 | Casutt ................. 623/17.15 |
| 2003/0171812 A1* | 9/2003 | Grunberg et al. ......... 623/17.11 |
| 2004/0097930 A1 | 5/2004 | Justis et al. |
| 2004/0102774 A1 | 5/2004 | Trieu |
| 2004/0133280 A1 | 7/2004 | Trieu |
| 2004/0260286 A1 | 12/2004 | Ferree |
| 2005/0192671 A1* | 9/2005 | Bao et al. ................. 623/17.14 |
| 2005/0197702 A1* | 9/2005 | Coppes et al. ............. 623/17.12 |
| 2007/0050032 A1* | 3/2007 | Gittings et al. ............ 623/17.12 |

* cited by examiner

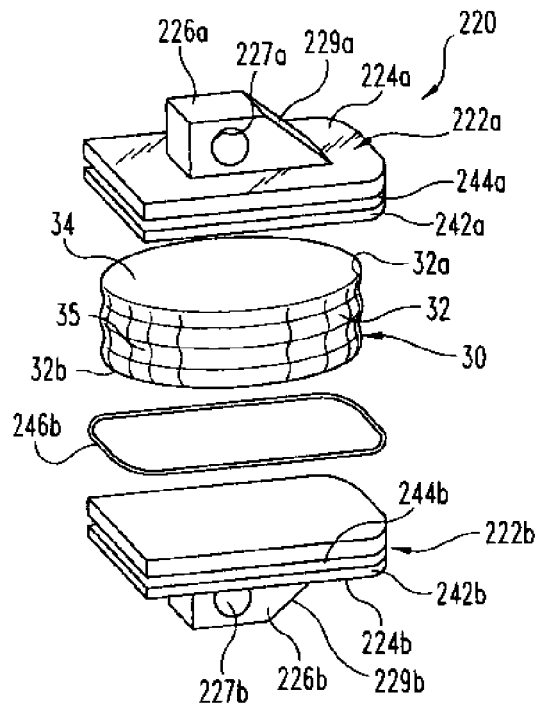
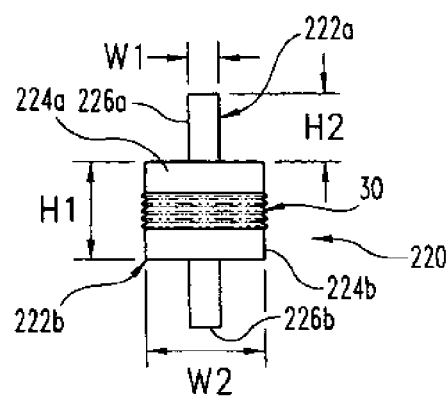
Fig. 10A
Fig. 10B
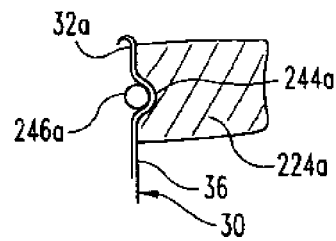
Fig. 11A
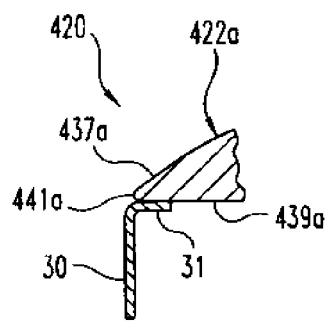
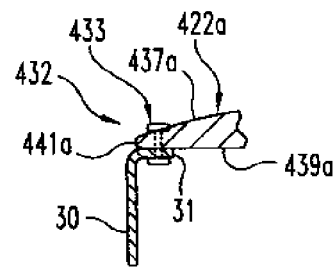
Fig. 11B  Fig. 11C

MINIMALLY INVASIVE SPINAL DISTRACTION DEVICES AND METHODS

CROSS REFERENCE TO RELATED APPLICATIONS

The present application is a continuation of co-pending U.S. patent application Ser. No. 11/645,825 filed Dec. 26, 2006, the contents of which are hereby incorporated by reference in their entirety.

BACKGROUND

With spinal deformities the spacing between adjacent vertebrae of the spine or the shape of a vertebra can be lacking or abnormal due to the condition of the disc space or one or more vertebrae prior to or due to conditions created during surgery. Restoration or repair of the spacing can require insertion of instruments to prepare the space for insertion of implants. The use of such instruments requires time to accommodate such insertion and additional exposure of the operative site to accommodate the instruments.

Implants have been developed that provide the ability to adjust the height or size of the implant after insertion. However, such adjustment can require manipulation of cumbersome and intricate instruments to insert the implant and to adjust the implant height. Such adjustment can also result in a non-uniform distribution of loads on the vertebral endplates or other bony structure at their interface with respective surfaces of the implant. Furthermore, in procedures involving a single implant, positioning of the implant while maintaining a minimally invasive access portal may require imbalanced support of the bony structure or structure by the implant. If multiple implants are provided to create a more balanced supporting condition, then multiple penetrations into the patient's body, or an increase in size of the surgical exposure, may be required to accommodate the multiple implant placement to the surgical site.

There remains a need for spinal stabilization systems and methods that minimize the surgical exposure and number of instruments used during spinal surgery, reduce the time for insertion of stabilization devices, and reduce the potential for loss of spinal stability.

SUMMARY

Systems and methods are provided for reducing the complexity and invasiveness of spinal stabilization and include an expandable device deliverable to a spinal disc space or other location. The device is delivered through a minimally invasive access portal and expanded in the disc space transversely to the central axis of the spinal column to distract the adjacent vertebrae, compress cancellous bone, or provide separation of adjacent bony portions.

According to one aspect, a spinal stabilization device includes a first member and a second member that each include a body extending along a longitudinal axis between a leading end and a trailing end and the bodies also have an outer surface and an opposite inner surface extending between the leading and trailing ends. The expandable device also includes a spacer member extending between the first and second members. The spacer member includes a collapsed configuration where the spacer member is substantially located between said first and second members with the first and second members adjacent one another and the leading ends of the bodies together form a round nose around the longitudinal axis. The spacer member is enlargeable to an expanded configuration where the first and second members are separated from one another.

According to one aspect, a spinal stabilization device includes first and second members that each has a body extending along a longitudinal axis between a leading end and a trailing end. The bodies further each include an outer surface and an opposite inner surface extending between the leading and trailing ends. The bodies also include a side connecting the outer and inner surfaces that define respective ones of first and second perimeters. The device also includes a spacer member extending between the first and second members. The spacer member includes a collapsed configuration where the spacer member is substantially located within at least one of the first and second perimeters of the first and second members and an expanded configuration wherein the spacer member includes a first portion that expands outwardly from the first and second perimeters in a first direction and a second portion that expands outwardly from the first and second perimeters in a second direction opposite the first direction.

In yet another aspect, a spinal stabilization device comprises a first member and a second member each with a rigid body extending along a longitudinal axis. The device further includes a spacer member extending between the first and second members. The spacer member includes a collapsed configuration for implantation in a spinal disc space of a spinal column where the spacer member and the first and second members together define a first shape when viewed in an axial plane of the spinal column. The spacer member also includes an expanded configuration where the spacer member defines a second shape when viewed in the axial plane that extends outwardly from the first and second members while the first and second members retain the first shape.

According to another aspect, a method for stabilizing a spinal disc space between adjacent vertebrae comprises: accessing the spinal disc space from an approach to the spinal column; positioning a device in the prepared spinal disc space along the approach, wherein the to device has an insertion configuration defining a first footprint in the spinal disc space when viewed in an axial plane of the spinal column; and expanding a spacer member of the device relative to upper and lower members of the device in the spinal disc space and transversely to the approach so that the expanded spacer member substantially occupies the spinal disc space and the upper and lower members engage the adjacent vertebrae while maintaining the first footprint.

According to another aspect, a method for restoring a vertebral body comprises: accessing the spinal disc space from an approach to the spinal column; positioning an expandable device in the vertebral body along the approach, wherein the expandable device has an insertion configuration defining a first footprint in the vertebral body; and expanding a spacer member of the expandable device to move rigid first and second members on opposite sides of the spacer member of the expandable device away from one another in the vertebral body and transversely to the approach so that the rigid first and second members compress cancellous bony in the vertebral body, wherein the spacer member is the only structure of the expandable device connecting the first and second members to one another in at least the expanded configuration.

In another aspect, a method for separating spinous processes comprises: accessing the space between spinous processes from an approach to the spinal column; positioning an expandable device between the spinous process along the approach, wherein the expandable device has an insertion configuration defining a first height between the spinous processes; and expanding a spacer member of the expandable device to move rigid first and second members of the expandable device on opposite sides of the spacer member away from one another transversely to the approach and into contact with respective ones of the spinous processes so that the rigid first and second members separate the spinous processes.

According to another aspect, and expandable device includes an expandable spacer member with a single rigid member along one side of the spacer member.

These and other aspects are also presented in the following description.

BRIEF DESCRIPTION OF THE DRAWINGS

FIG. 10A is an exploded perspective view of a collapsed expandable device according to another embodiment.

FIG. 10B is an end elevation view of the device of FIG. 10A.

FIGS. 11A-11C show various attachment means for securing the spacer member to the respective first and second members.

DESCRIPTION OF THE ILLUSTRATED EMBODIMENTS

Figure 1A:
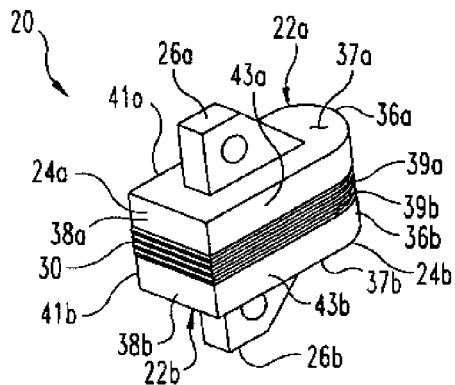
FIGS. 1A and 1B are perspective views of a collapsed and expanded expandable device, respectively, for spinal stabilization according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated herein are contemplated as would normally occur to one skilled in the art to which the invention relates.

There are provided systems and methods for positioning and deploying an expandable device in or between bony structures of a spinal column segment to provide balanced support of the adjacent vertebrae while minimizing the size and number of approaches and size and number of devices implanted. Such systems include instruments for delivering the expandable devices to the operative site and expanding the expandable devices in situ. Such expansion distracts or maintains distraction of adjacent vertebrae when positioned in an intervertebral space, restores deformed spinal column segments, and provides immediate and long-term support of one or more bony structures.

According to one embodiment, upon positioning the expandable device at the operative site, the device is expanded to deploy and expand the expandable device at the operative site. Such deployment and expansion of the expandable device is operable, for example, to position the device to occupy all or substantially all of the intervertebral space to provide balanced support of the adjacent vertebrae. Expansion of the device is further operable to distract adjacent vertebrae to provide a desired disc space height, although distraction of the disc space prior to expansion of the device is also contemplated.

The systems and methods are employable in minimally invasive surgical approaches to the spine. Such approaches include anterior, posterior, transforaminal, postero-lateral, lateral, oblique, transpedicular and other approaches to the disc space. The approaches may be uni-portal or multi-portal in nature and directed to any portion of the spinal column segment, including the sacral, lumbar, thoracic, and cervical regions. The systems methods are employable with any viewing system to assist in monitoring placement of the expandable device in the disc space and the expansion of the device with the distraction instrument. Examples of suitable viewing systems include fluoroscopic, endoscopic, microscopic, CT scan, X-ray, image-guided, and naked eye visualization systems.

Figure 1B:
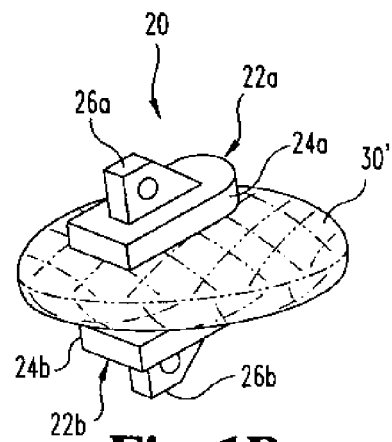

Referring now to FIGS. 1A and 1B, there is shown a first embodiment of an expandable device 20. In this embodiment, expandable device 20 includes a body positionable in a spinal disc space that includes a first member 22a positionable along one endplate of a first vertebra and a second member 22b positionable along the endplate of an adjacent second vertebra. First member 22a extends along a longitudinal axis between a distal leading insertion end 36a and a proximal trailing end 38a. First member 22a also includes an outer surface 37a and an opposite inner surface 39a. Opposite sides 41a, 43a extend between outer and inner surfaces 37a, 39a between leading and trailing ends 36a, 38a. Sides 41a, 43a and ends 36a, 38a define a first perimeter about first member 22a.

Second member 22b extends along a longitudinal axis between a distal leading insertion end 36b and a proximal trailing end 38b. Second member 22b also includes an outer surface 37b and an opposite inner surface 39b. Opposite sides 41b, 43b extend between outer and inner surfaces 37b, 39b and also between leading and trailing ends 36b, 38b. Sides 41b, 43b and ends 36b, 38b define a second perimeter about second member 22b. Ends 36a, 36b are convexly rounded between the respective sides 41a, 43a or sides 41b, 43b. Outer surfaces 37a, 37b are flat or generally planar as shown to provide a plate-like body, although non-planar configurations are also contemplated. The first and second perimeters define a generally rectangular shape with a rounded leading end. Other shapes for the perimeters are also contemplated, including oval, square, circular, polygonal, and irregularly shape perimeters.

A spacer member 30 is positioned between first member 22a and second member 22b of expandable device 20. Spacer member 30 is coupled to first and second members 22a, 22b and also extends between distal leading ends 36a, 36b and trailing ends 38a, 38b. In one embodiment, the spacer member 30 is the only structure connecting first and second members 22a, 22b and the first and second members 22a, 22b have a rigid body structure, minimizing the footprint of the device and its complexity. In FIG. 1 spacer member 30 is shown in a collapsed or unexpanded state where spacer member 30 is confined or substantially located within the first and second perimeters of first and second members 22a, 22b. In FIG. 1B space member 30 is expanded to an expanded state indicated by spacer member 30'. In the expanded state, spacer member 30' extends substantially outwardly from the first and second perimeters to provide an expanded footprint when viewed in the axial plane that differs from the footprint provided by the first and second members 22a, 22b.

Referring now to FIGS. 2A-2D, there is shown a first embodiment of an expandable device 420. In this embodiment, expandable device 420 includes a body positionable in a spinal disc space that includes a first member 422a positionable along one endplate of a first vertebra and a second member 422b positionable along the endplate of an adjacent second vertebra. First member 422a extends along a longitudinal axis 421 between a distal leading insertion end 436a and a proximal trailing end 438a. First member 422a also includes an outer surface 437a and an opposite inner surface 439a. Opposite sides 441a, 443a extend between outer and inner surfaces 437a, 439a between leading and trailing ends 436a, 438a. Sides 441a, 443a and ends 436a, 438a define a first perimeter about first member 422a.

Second member 422b extends along longitudinal axis 421 between a distal leading insertion end 436b and a proximal trailing end 438b. Second member 422b also includes an outer surface 437b and an opposite inner surface 439b. Opposite sides 441b, 443b extend between outer and inner surfaces 437b, 439b and also between leading and trailing ends 436b, 438b. Sides 441b, 443b and ends 436b, 438b define a second perimeter about second member 422b. The first and second perimeters define a generally rectangular shape with a rounded leading end. Other shapes for the perimeters are also contemplated, including oval, square, circular, polygonal, and irregularly shape perimeters.

Figure 2A:
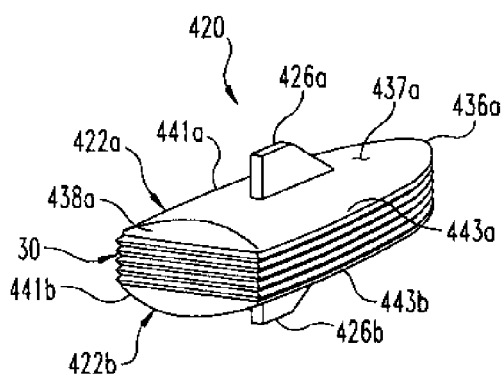
FIGS. 2A and 2B are perspective views of a collapsed and expanded expandable device, respectively, for spinal stabilization according to another embodiment.
Figure 2B:
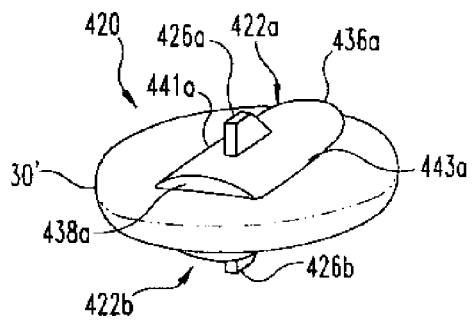
Figure 2C:
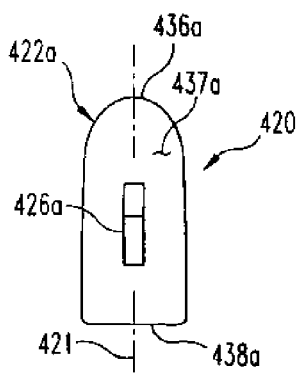
FIGS. 2C and 2D are a plan view and an elevation view, respectively, of the expandable device of FIGS. 2A and 2B.

Outer surfaces 437a, 437b are convexly curved between the respective opposite sides 441, 443a and opposite sides 441b, 443b. Furthermore, as shown in FIG. 2C, leading end nose 436a is convexly rounded between opposite sides 441a, 443a transversely to longitudinal axis 421. Leading end nose 436b is also similarly rounded. In further reference to FIG. 2D, leading end noses 436a, 436b can be convexly rounded between the respective outer surfaces 437a, 437b and inner surfaces 439a, 439b. The dual convexity of leading ends 436a, 436b provides a bullet shaped tip in the collapsed configuration that facilitates insertion into the spacer between vertebrae or other bony structures. Outer surfaces 437a, 437b can be flat in the direction extending along longitudinal axis 421, or are convexly rounded in the direction along longitudinal axis 421 as shown.

Figure 2D:
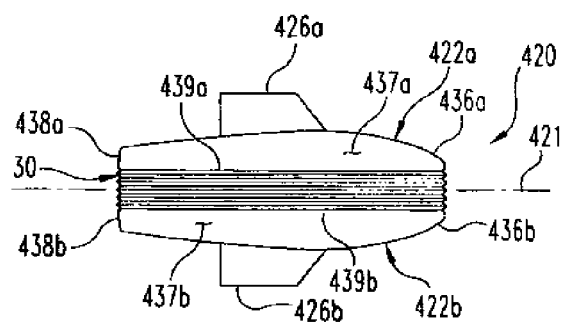

Spacer member 30 is positioned between first member 422a and second member 422b of expandable device 420. Spacer member 30 is coupled to first and second members 422a, 422b and also extends between distal leading ends 436a, 436b and trailing ends 438a, 438b. In one embodiment, the spacer member 30 is the only structure connecting first and second members 422a, 422b and the first and second members 422a, 422b have a rigid body structure, minimizing the footprint of the device and its complexity. In FIGS. 2A and 2D, spacer member 30 is shown in a collapsed or unexpanded state where spacer member 30 is confined or substantially located within the first and second perimeters of first and second members 422a, 422b. In FIG. 2B space member 30 is expanded to an expanded state indicated by spacer member 30'. In the expanded state, spacer member 30' extends substantially outwardly from the first and second perimeters to provide an expanded footprint when viewed in the axial plane that differs from the footprint provided by the first and second members 422a, 422b.

First members 22a, 422a are each provided with at least one engagement member 26a, 426a, and second members 22b, 422b are also each provided with at least one engagement member 26b, 426b. Engagement members 26a, 426a, 26b, 426b are engageable with bony tissue of the vertebrae, and are shown in the form of keels or fins. In the illustrated embodiment, engagement members 26a, 26b include apertures 27a, 27b, respectively, to receive bone growth. Other embodiments contemplate engagement members in the form of teeth, spikes, ridges, threads, barbs, knurlings, protrusions, and combinations thereof, for example. It is further contemplated that the outer surfaces of first members 22a, 422a and second members 22b, 422b can be smooth, or provide auxiliary fixation surfaces, porous surfaces, bone growth material, therapeutic agents, or features can be provided thereon. First members 22a, 422a and second members 22b, 422b may further include one or more openings, apertures, recesses, detents or other features to receive bone ingrowth.

First members 22a, 422a and second members 22b, 422b are movable away from one another from an unexpanded configuration, as shown in FIG. 1A and in FIG. 2A, respectively, to an expanded configuration, as shown in FIG. 1B and FIG. 2b. In the unexpanded configuration, spacer member 30 has a reduced height between first member 22a, 422a and second member 22b, 422b and a footprint that is substantially confined to the footprint of first members 22a, 422a and second members 22b, 422b such as shown in FIGS. 1A and 2A. In the expanded configuration, spacer member 30' has a greater height between first member 22a, 422a and second member 22b, 422b and a footprint that extends outwardly from first members 22a, 422a and second members 22b, 422b to replicate or substantially occupy the disc space. In one embodiment, the unexpanded height will allow expandable device 20, 420 to be inserted, for example, in a disc space between adjacent vertebral bodies that is collapsed or otherwise deformed. The expanded height corresponds to a separation height between first members 22a, 22b and second members 22b, 422b required to provide a desired disc space height between adjacent vertebrae. When expanded, spacer member 30' has an increased height and increased footprint in the disc space that replicates the height and footprint of the spinal disc space. In another embodiment, spacer member 30 has an unexpanded height that is substantially equal to or slightly less than its expanded height and no or minimal distraction is provided by expanded spacer member 30'.

Spacer member 30 is in the form of an enlargeable structure having a collapsed configuration, as shown in FIGS. 1A and 2A, and an enlarged or expanded configuration, as shown in FIGS. 1B and 2B. In one embodiment, spacer member 30 is elastic. In another embodiment, spacer member 30 is non-elastic. Spacer member 30 is provided with a hollow interior with one or more chambers or cavities in communication with a lumen through which fluid or material can be supplied into spacer member 30 to enlarge it. After delivery of expandable device 20 to the operative site, spacer member 30 is enlarged to provide an enlarged spacer member 30' and maintain separation of first and second members 22a, 22b as shown in FIG. 1B or first and second members 422a, 422b as shown in FIG. 2B. In the illustrated embodiment, spacer member 30 includes a single expandable element, although multiple expandable elements are also contemplated to provide alternate enlargement characteristics. For example, one expandable element of spacer member 30 could include a first size to extend from one side of first and second members and another expandable element having a second size to extend from a second side of first and second members. Such expandable elements expand uni-directionally from first and second members.

It is contemplated that spacer member 30 post-operatively maintains expandable device 20, 420 in an expanded condition. Accordingly, spacer member 30 is enlarged or expanded with, for example, bone growth material, flexible material, or other suitable filler material to facilitate bone growth or preserve motion of the intervertebral space through the expanded device 20, 420. Spacer member 30 may be fabricated from porous material, resorbable material, or other suitable material to allow bone growth through the cavity of the expanded device. In another embodiment, spacer member 30 is expanded with a polymer that is flowable into expandable element and thereafter polymerizes or solidifies to form an elastic core between first and second members of the expandable devices 20, 420 and the adjacent vertebrae.

Spacer member 30 includes a size and shape that matches the size and shape of the intradiscal space in its expanded configuration 30', although non-matching configurations are also contemplated. In the expanded configuration, spacer member 30' applies expansion forces to first and second members 22a, 22b or the first and second members 422a, 422b to force or maintain engagement members 26a, 26b or engagement members 426a, 426b in engagement with the adjacent vertebral body.

First members 22a, 422a and second members 22b, 422b and/or spacer member 30 may to be provided with one or more openings, windows, porous structure or other structure that allows communication therethrough and the adjacent bony structure to facilitate bone ingrowth. The expandable devices may include a single cavity or be provided with multiple cavities in the spacer member. The spacer member could be resorbable so that over time the outer shell defining the spacer member resorbs and material within the shell of the spacer member remains to provide the support function. The spacer member could also be porous to permit bone growth therein. Other embodiments contemplate that the spacer member is solid, or made from a non-resorbable material.

Spacer member 30 is made from any suitable material capable of withstanding the pressure supplied to enlarge or expand spacer member 30 in situ. Examples include various polymeric materials, including polyethylene, terephthalates, polyolefins, polyurethanes, nylon, polyvinyl chloride, silicone or other suitable material. The material comprising spacer member 30 can be reinforced with woven or non-woven textile materials. Examples of suitable reinforcement materials include those that are polymeric and metallic in nature.

The first members 22a, 422a and second members 22b, 422b are made from any bio-compatible material, including metals, polymers and composites. Examples of metals include titanium and titanium alloys; nickel titanium alloys; stainless steel; and cobalt chrome alloys. Examples of polymers include polyaryletherketone; polyetheretherketone; polysulfone; polyolefin; polyethylene; tyrosine-based polycarbonate; polyester; polylactide; polyglicolide; polyorthoester; polyphosphazene; polyhydroxylbutyrate; and polyhydroxylvalerate, for example. Examples of composites include carbon filled composites; hydroxy-apetite filled composites; bioactive glass filled composites; and cortical bone chip filled composites, for example.

Figure 3A:
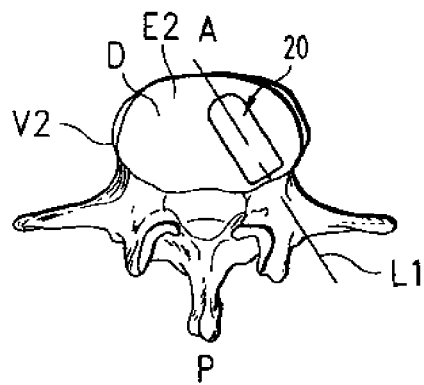
FIGS. 3A and 3B are a plan view and an elevation view, respectively, of a spinal column segment with the collapsed expandable device of FIG. 1 positioned in a disc space thereof in a postero-lateral approach.
Figure 3B:
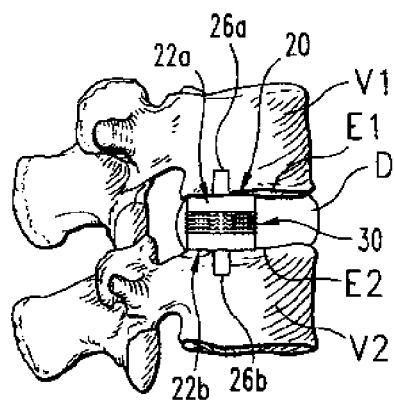

One example of a surgical technique employing expandable devices and delivery instruments in an intervertebral space will now be discussed with reference to FIGS. 3A through 4B and expandable device 20, it being understood that expandable device 420 could also be employed. Referring now to FIGS. 3A and 3B, there is shown a spinal column segment including a lower vertebra V1 having an endplate E1, an upper vertebra V2 having an endplate E2, and a disc space D therebetween. The anterior side of the spinal column is indicated as side A and the posterior side is indicated as side P. An approach to disc space D is defined along axis L1, which is oriented obliquely to the sagittal plane to provide for transforaminal positioning of expandable device 20 in a posterolateral approach. First and second members 22a, 22b also extend along axis L1.

Figure 4A:
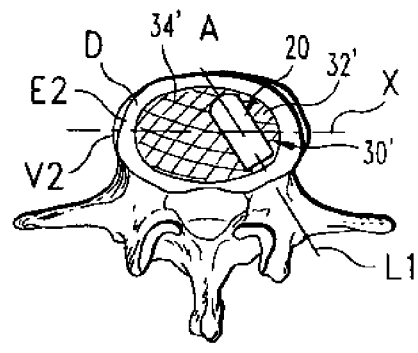
FIGS. 4A and 4B are a plan view and an elevation view, respectively, with the expandable device of FIG. 1 expanded in the disc space of the spinal column segment.
Figure 4B:
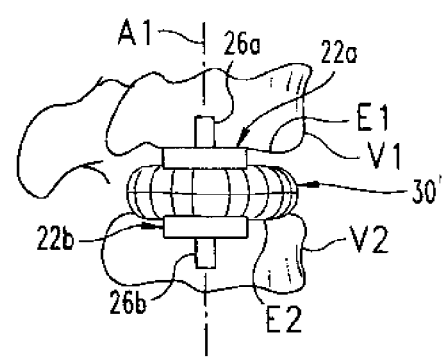

After appropriate discectomy, endplate preparation, and distraction as needed and if desired, expandable device 20 is delivered along approach L1 and positioned in disc space D with any suitable delivery or inserter instrument with spacer member 30 in an unexpanded state, as shown in FIGS. 3A and 3B. First and second members 22a, 22b and spacer member 30 have a reduced profile and footprint to allow insertion through a minimally invasive access portal positioned along approach L1. Spacer member 30 is thereafter expanded transversely to central axis A1 of the spinal column and relative to first and second members 22a, 22b to form expanded spacer member 30', as shown in FIGS. 4A and 4B.

In the expanded configuration, engagement members 26a, 26b engage the respective vertebrae V1, V2 through endplates E1, E2. In addition, the footprint of spacer member 30, when viewed in the axial plane as shown in FIG. 4A, is expanded to occupy all or substantially all of disc space D. Expanded spacer member 30' includes a first lateral portion 32' extending outwardly from the perimeter of first and second members 22a, 22b in a first direction from approach L1. Spacer member 30' also includes a second lateral portion 34' extending outwardly from the perimeter of first and second members 22a, 22b in a direction opposite first lateral portion 32'.

Spacer member 30' expands eccentrically from first and second members 22a, 22b primarily along an axis X1 that is obliquely oriented to axis L1 to maintain portions 32', 34' within the disc space D without protruding anteriorly or posteriorly from disc space D. First portion 32' has a size and shape that is adapted to conform to the size and shape of disc space D in the side located laterally of approach L1, and second portion 34' has a size and shape that is adapted to conform to the size and shape of disc space D on the side thereof located medially of approach L1. When viewed in the axial plane, the expanded spacer member 30' have an oval shape, while first and second members 22a, 22b maintain a generally rectangular configuration when viewed in the axial plane.

It is contemplated that receiving areas or channels are formed in endplates E1, E2 to receive bodies 24a, 24b and/or engagement members 26a, 26b, although procedures that do not create channels or receiving areas are also contemplated. The receiving areas can be sized and shaped to match the outer surface profile of the portion of the expandable device to be positioned therein. The receiving areas may be formed by any one or combination of reaming, scraping, cutting, or chiseling. The receiving areas are sized and shaped to match the outer surface profile of the portion of the expandable device to be positioned therein. In the illustrated embodiment, first and second members 22a, 22b include bodies 24a, 24b that each has a square or rectangular cross-section. Other embodiments contemplate cross-sections that are circular or arcuate in shape. Still further it is contemplated that receiving areas are not formed, and the expandable device is placed into contact directly with the cortical bone of the endplates or with the endplates otherwise prepared. Furthermore, the engagement members 26a, 26b can include a self-cutting configuration.

In the embodiments for the expandable device discussed below, it is contemplated that the spacer members include any one or combination of the features discussed herein for spacer member 30. In addition, the first and second members between which the spacer member extends include any one or combination of the features discussed herein for the first and second members of either of the expandable devices 20, 420.

Figure 5A:
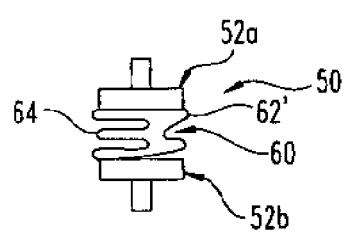
FIGS. 5A and 5B are an elevation view of a collapsed and expanded device, respectively, for positioning in a spinal disc space in an approach offset from the sagittal plane.
Figure 5B:
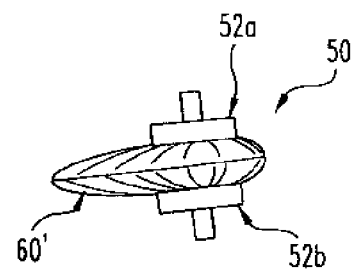

In another embodiment of expandable device 20, there is shown expandable device 50 in FIGS. 5A and 5B. Expandable device 50 includes first and second members 52a, 52b and a spacer member 60 therebetween. Spacer member 60 is shown in FIG. 5A in a collapsed condition where its sides 62, 64 are folded one on top of the other and confined or located within the perimeters of first and second members 52a, 52b to provide a minimized footprint for insertion into the disc space. In the expanded configuration, spacer member 60' projects outwardly from the perimeters defined by first and second members 52a, 52b into the surrounding disc space when implanted.

Figure 6A:
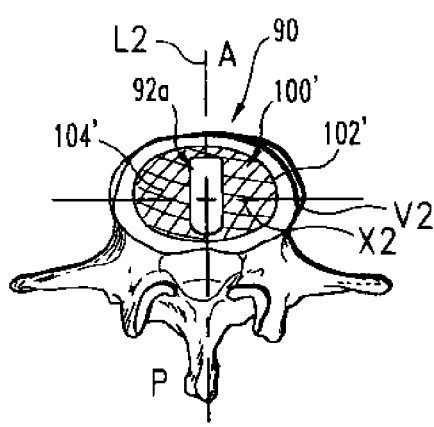
FIGS. 6A and 6B are a plan view and an elevation view, respectively, of a spinal column segment with another embodiment expanded device positioned therein in an anterior approach.
Figure 6B:
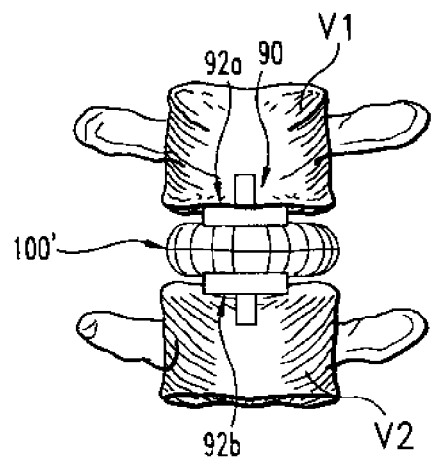

Another example of a surgical technique employing expandable devices and delivery instruments in an intervertebral space will now be discussed with reference to FIGS. 6A and 6B. An approach to disc space D is defined along axis L2, which is oriented along or substantially parallel to the sagittal plane to provide for an anterior approach and anterior to posterior positioning of expandable device 90 from the anterior approach L2. After appropriate discectomy, endplate preparation, and distraction as needed and if desired, expandable device 90 is delivered along approach L2 and positioned in disc space D with any suitable delivery or inserter instrument with spacer member 100' in an unexpanded state (not shown) with first and second members 92a, 92b and spacer member 100' having a reduced profile and footprint to allow insertion through a minimally invasive access portal positioned along approach L2. In FIGS. 6A and 6B, spacer member 100' is expanded relative to first and second members 92a, 92b.

In the expanded configuration, engagement members of the first and second members 92a, 92b engage the respective vertebrae V1, V2 through endplates E1, E2. In addition, the footprint of spacer member 100', when viewed in the axial plane of the spinal column as shown in FIG. 6A, occupies all or a substantial portion of disc space D. Expanded spacer member 100' includes a first lateral portion 102' extending outwardly from the perimeter of first and second members 92a, 92b in a first direction from approach L2. Spacer member 100' also includes a second lateral portion 104' extending outwardly from the perimeter of first and second members 92a, 92b in a direction opposite first lateral portion 102'. Spacer member 100' expands concentrically relative to first and second members 92a, 92b along an axis X2 that is orthogonally or substantially orthogonally oriented to axis L2 to form an oval shape, while first and second members 92a, 92b maintain a generally rectangular shape. First and second lateral portions 102', 104' each have a size and shape that is adapted to conform to the size and shape of disc space D in the respective lateral side of approach L2. First and second lateral portions 102', 104' have the same size and shape. Alternatively, the sizes and shapes can be different in procedures where, for example, approach L2 is offset from the sagittal plane.

Figure 7A:
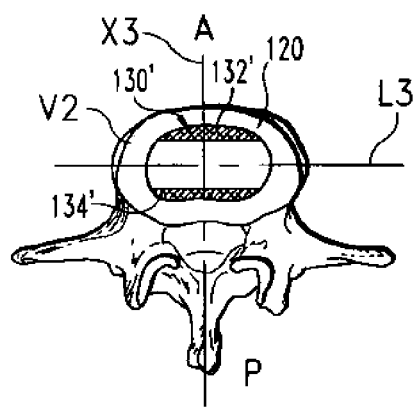
FIGS. 7A and 7B are a plan view and an elevation view, respectively, of a spinal column segment with another embodiment expanded device positioned therein in a lateral approach.
Figure 7B:
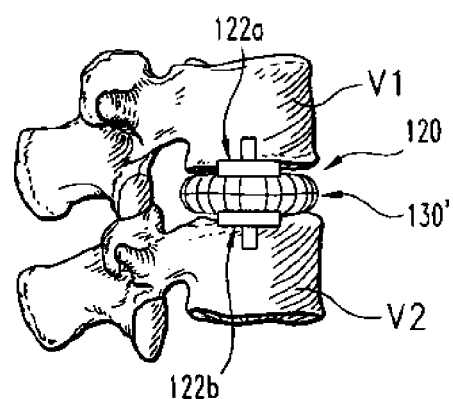

Another example of a surgical technique employing expandable devices and delivery instruments in an intervertebral space will now be discussed with reference to FIGS. 7A and 7B. An approach to disc space D is defined along axis L3, which is oriented along or substantially parallel to the coronal plane to provide for a lateral approach and medial-lateral positioning of expandable device 120 from the lateral approach L3. After appropriate discectomy, endplate preparation, and distraction as needed and if desired, expandable device 120 is delivered along approach L3 and positioned in disc space D with any suitable delivery or inserter instrument with spacer member 130' in an unexpanded state (not shown) with first and second members 122a, 122b and spacer member 130' having a reduced profile and footprint to allow insertion through a minimally invasive access portal positioned along approach L3. In FIGS. 7A and 7B, spacer member 130' is expanded relative to first and second members 122a, 122b.

In the expanded configuration, engagement members of the first and second members 122a, 122b engage the respective vertebrae V1, V2 through endplates E1, E2. In addition, the footprint of spacer member 130', when viewed in the axial plane of the spinal column as shown in FIG. 7A, occupies all or a substantial portion of disc space D. Expanded spacer member 130' includes a first anterior portion 132' extending outwardly from the perimeter of first and second to members 122a, 122b in a first direction from approach L3. Spacer member 130' also includes a second posterior portion 134' extending outwardly from the perimeter of first and second members 122a, 122b in a direction opposite first anterior portion 132'. Spacer member 130' expands concentrically relative to first and second members 122a, 122b along an axis X3 that is orthogonally or substantially orthogonally oriented to axis L3. The expanded spacer member 130' has a generally circular shape when expanded and first and second members 122a, 122b maintain a substantially rectangular shape. First and second portions 132', 134' each have a size and shape that is adapted to conform to the size and shape of the respective portion of disc space D located on the respective anterior and posterior side of approach L3. First and second anterior and posterior portions 132', 134' can have the same size and shape, or can be different in procedures where, for example, approach L3 is offset from the coronal plane.

Figure 8:
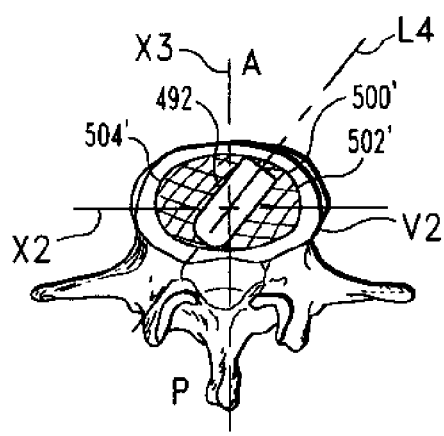
FIG. 8 is a plan view of a spinal column segment with another embodiment expanded device positioned therein in an antero-lateral approach.

Another example of a surgical technique employing expandable devices and delivery instruments in an intervertebral space will now be discussed with reference to FIG. 8. An approach to disc space D is defined along axis LA, which is oriented obliquely to sagittal plane X3 to provide for an antero-lateral approach LA. After appropriate discectomy, endplate preparation, and distraction as needed and if desired, expandable device 490 is delivered along approach L4 and positioned in disc space D with any suitable delivery or inserter instrument with spacer member 500' in an unexpanded state (not shown) and the expandable device 490 having a reduced profile and footprint to allow insertion through a minimally invasive access portal positioned along approach L4.

In the expanded configuration, engagement members of the first and second members 492 (only one shown) engage the respective vertebrae through their respective endplates. In addition, the footprint of spacer member 500', when viewed in the axial plane of the spinal column as shown in FIG. 8, forms an oval shape that occupies all or a substantial portion of disc space D. Expanded spacer member 500' includes a first lateral portion 502' extending outwardly from the perimeters of first and second members 492 in a first direction from approach L4. Spacer member 500' also includes a second lateral portion 504' extending outwardly from the perimeters of first and second members 492 in a direction opposite first lateral portion 502'. Spacer member 500' expands eccentrically from first and second members 492 along an axis X2 that is orthogonally or substantially orthogonally oriented to sagittal plane X3 and obliquely oriented to antero-lateral approach L4. First and second lateral portions 102', 104' each have a size and shape that is adapted to conform to the size and shape of disc space D along the respective side of the antero-lateral approach L4.

Figure 9:
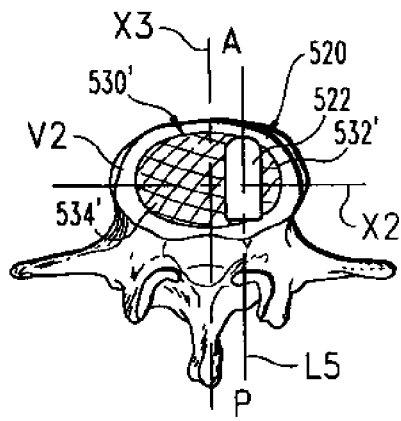
FIG. 9 is a plan view of a spinal column segment with another embodiment expanded device positioned therein in a posterior approach.

Another example of a surgical technique employing expandable devices and delivery instruments in an intervertebral space will now be discussed with reference to FIG. 9. An approach to disc space D is defined along axis L5, which is oriented from the posterior side P in a posterior approach that is offset laterally from sagittal plane X3. Delivery from the postero-lateral approach can involve retraction of the dura, but avoid removal of the facet as typically required in a postero-lateral approach. After appropriate discectomy along the approach L5, endplate preparation, and distraction as needed and if desired, expandable device 520 is delivered along approach IA and positioned in disc space D with any suitable delivery or inserter instrument with spacer member 530' in an unexpanded state (not shown) and the expandable device 520 having a reduced profile and footprint to allow insertion through a minimally invasive access portal positioned along posterior approach L5.

In the expanded configuration, engagement members of the first and second members 522 (only one shown) engage the respective vertebrae through their respective endplates while maintaining a rectangular shape. In addition, the footprint of spacer member 530', when viewed in the axial plane of the spinal column as shown in FIG. 9, forms an oval shape that occupies all or a substantial portion of disc space D. Expanded spacer member 530' includes a first lateral portion 532' extending outwardly from the perimeters of first and second members 522 in a first direction from approach L5. Spacer member 530' also includes a second lateral portion 534' extending outwardly from the perimeters of first and second members 522 in a direction opposite first lateral portion 532'. Spacer member 530' expands eccentrically along an axis X2 that is orthogonally or substantially orthogonally oriented to the posterior approach L5 and the sagittal plane X3. First and second lateral portions 532', 534' each have a size and shape that is adapted to conform to the size and shape of disc space D along the respective side of the posterior approach L5.

In yet other embodiments, the spacer member extends transversely to the approach in only one direction laterally from the respective first and second members. Such embodiments can be employed to provide uni-lateral distraction of the disc space on one side of the disc space. For example, distraction can be provided by expansion on one side of the sagittal plane to provide correction of spinal curvature as a result of scoliosis. In another embodiment, the spacer 1a member expands from both sides of the first and second members, but one of the lateral portions of the expanded spacer member has a height greater than the other of the expanded lateral portions to provide greater distraction of the disc space at the targeted location. In still other embodiments, the spacer member expands between the first and second members to provide a greater height to the expanded device, but does not expand laterally from the first and second members.

Referring now to FIG. 10A, there is shown another embodiment expandable device 220 in an exploded perspective view. Expandable device 220 includes first and second members 222a, 222b and expandable spacer member 30 between first and second members 222a, 222b. First and second members 222a, 222b each include a body 224a, 224b having a flat, plate-like configuration and with engagement members 226a, 226b extending outwardly therefrom. Engagement members 226a, 226b are in the form of axially elongated keels or fins, and can include an aperture 227a, 227b. Engagement members 226a, 226b are provided with a forward or leading end 229a, 229b that is sloped to facilitate insertion into the respective vertebral body.

Spacer member 30 includes body 32 having a central chamber 34 and side 35 extending around chamber 34 between a first end 32a and an opposite second end 32b. Side 35 extends along the respective sides 242a, 242b of bodies 224a, 224b. Sides 242a, 242b each include a groove 244a, 244b extending thereabout. Bands 246a, 246b (FIG. 11A) extend circumferentially about the respective sides 242a, 242b. Spacer member 30 is secured to first and second members 222a, 222b with respective ones of the bands 246a, 246b positioned to crimp or frictionally engage side 35 in the respective grooves 244a, 244b.

FIG. 10B shows expandable device 220 in an end elevation view. Expandable device 220 includes a height H1 between the opposite outer surfaces of bodies 224a, 224b. Engagement members 226a, 226b each extend a height H2 from the respective outer surface of bodies 224a, 224b. In one embodiment, height H1 is about twice as great as height H2 in the expanded configuration. Other embodiments contemplate other ratios between height H1 and height H2. Bodies 224a, 224b also include a width W1, and engagement members 226a, 226b include a width W2. Width W1 can be about five times greater than width W2, although other ratios of widths W1 to W2 are also contemplated.

Other embodiments contemplate other attachment means for securing the spacer member to one or both of the first and second members. For example, FIG. 11B shows a portion of first member 422a of expandable device 420 and spacer member 430 in section view. First member 422a includes an inner surface 439a opposite the outer bone contacting surface 437a. Spacer member 430 includes an end 431 secured to the inner surface 439a. End 431 is secured to inner surface 439a via an adhesive or an epoxy type substance, through a fusion or welded-type connection, or by over-molding or slip fitting the spacer member into a receptacle in first member 422a. Spacer member 430 could alternatively or additionally be secured to one or more of the side 441a or outer surface 437a of first member 422a. Second member 422b could also be secured by the same attachment means to spacer member 430, or by a different attachment means.

FIG. 11C shows another attachment means 432 in the form of a fastener 433. Fastener 433 is in the form of a rivet, tack, pin, screw, bolt, suture, thread, wire, or other interwoven device. Spacer member 430 could alternatively or additionally be secured to one or more of the side 441a or outer surface 437a of first member 422a. Second member 422b could also be secured by the same attachment means to spacer member 430, or by a different attachment means.

Figure 12A:
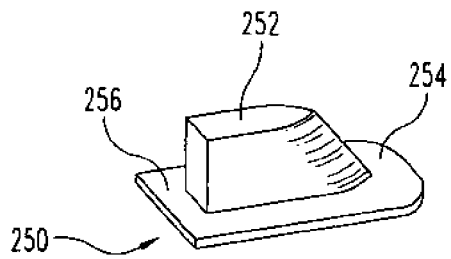
FIG. 12A is a perspective view one embodiment of an engagement member of an expandable device.
Figure 12B:
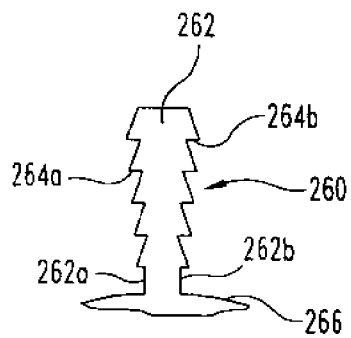
FIGS. 12B and 12C are elevation views of other embodiment engagement members of an expandable device.
Figure 12C:
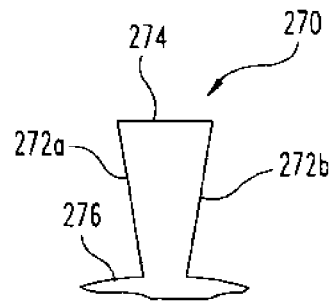

FIGS. 12A-12C show various embodiment engagement members. In FIG. 12A, engagement member 250 includes an elongated body 252 that extends outwardly from a body 256 of a first or second member of an expandable device. Body 252 includes a sloped or inclined leading insertion edge 254 that is pointed in a manner similar to a knife blade to facilitate passage through bony tissue. FIG. 12B illustrates an engagement member 260 with sides 262a, 262b extending from body 266 that have barbed, ratcheted or serrated edges 264a, 264b extending therealong. The barbed edges 264a, 264b engage the bony tissue and provide a ratcheting type effect to provide secure engagement and resist movement of the vertebrae away from one another. FIG. 12C illustrates another embodiment engagement member 270 that includes sides 272a, 272b that are tapered from an outer end 274 toward body 276 of the respective first or second member of the expandable device. The tapered sides 272a, 272b provide wedge or dovetail effect with a correspondingly shaped portion in the vertebral body to provide secure engagement with the vertebra by resisting pull-out and movement of the vertebrae away from one another.

Figure 13A:
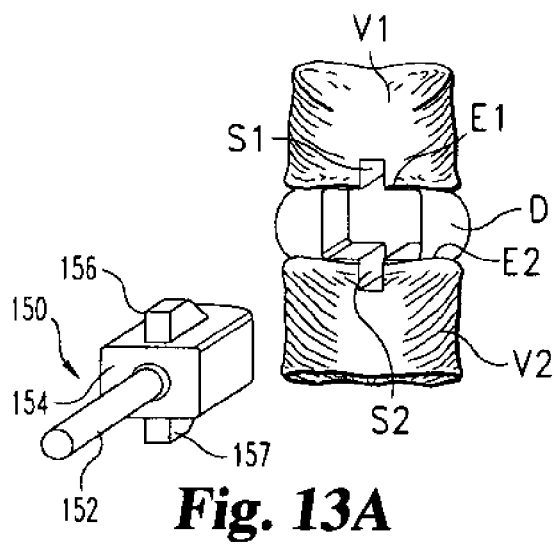
FIGS. 13A-13E show various steps and instruments in a surgical method for preparing an intervertebral space to receive an expandable device and for inserting the expandable device into the prepared intervertebral space.

In FIGS. 13A-13E, various steps of a procedure for preparing vertebrae V1, V2 to receive an expandable device will be discussed. The illustration will be provided with expandable device 20, it being understood that the other expandable device embodiments could be inserted after similar vertebral preparations along the respective approaches. In FIG. 13A, chisel 150 is shown in an approach to disc space D, such as along approach L1. Chisel 150 includes an elongated shaft 152 extending between a handle (not shown) or other proximal structure and a distal head 154. Head 154 includes upper and lower cutting members 156, 157 extending therefrom. Head 154 is positioned into disc space D so that cutting members 156, 157 extend into and cut slots S1 and S2 in the respective vertebrae V1 and V2.

Figure 13B:
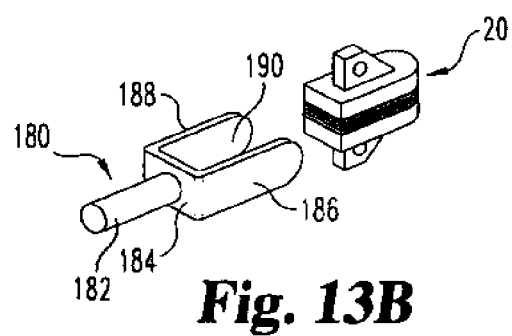
Figure 13C:
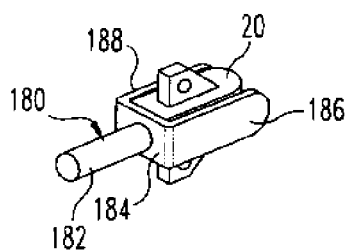
Figure 13D:
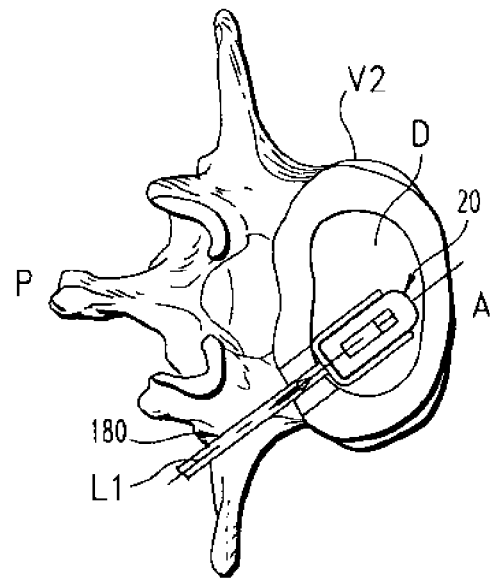
Figure 13E:
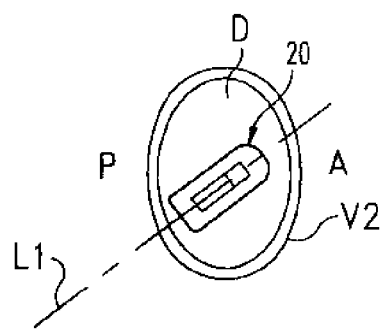

In FIGS. 13B and 13C, there is shown an impactor 180 having an elongated shaft 182 extending from a proximal handle (not shown) or other structure to a distal mounting member 184. Mounting member 184 includes a pair of arms 186, 188 spaced from one another to form a receptacle 190 therebetween. Receptacle 190 is sized and shaped to receive expandable device 20, or any other expandable device embodiment discussed herein, as shown in FIG. 13C. Arms 186, 188 extend along first and second members 22a, 22b, and have a height that corresponds to the height H1 between the outer surfaces of first and second members 22a, 22b. Engagement members 26a, 26b extend outwardly from the upper and lower edges of arms 186, 188 for insertion into the respective vertebrae as the upper and lower edges move along the respective vertebral endplates E1, E2. The leading ends of arms 186, 188 are rounded or tapered to facilitate insertion into disc space D and provide distraction or recapitulation of the vertebrae V1, V2 upon placement therebetween, as shown in FIG. 13D. After placement of expandable device 20 in the desired location in disc space D, impactor 180 is removed along the same approach L1 in which it was positioned to disc space D, leaving the unexpanded expandable device 20 in disc space D as shown in FIG. 13E.

Figure 14:
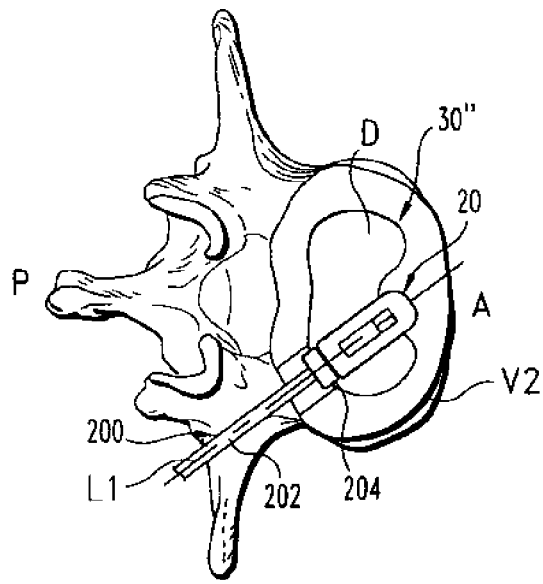
FIG. 14 shows the expandable device implanted in FIGS. 13A-13E connected with an expansion instrument and with the expandable device partially expanded.

In FIG. 14 there is shown the implanted expandable device 20 with spacer member 30" in a partially expanded condition. In order to expand spacer member 30, an injection instrument 200 is coupled to an injection port of expandable device 20. Injection instrument 200 includes a delivery lumen 202 and a distal tip 204. Material is delivered through one or more passages of lumen 202 and into spacer member 30 through its connection location with distal tip 204. Injection instrument 200 is inserted and engaged to expandable device 20 along approach L1 or through an alternate approach.

In another procedure, distraction is provided by the impactor or other inserter instrument, and is maintained after implant insertion and during withdrawal of the impactor from the disc space. For example, the impactor 180 provides distraction during insertion of the expandable device. The impactor is coupled to the expandable device and includes a material delivery lumen that can deliver material to the spacer member. As the impactor is withdrawn, material is delivered through the impactor to the spacer member so that expansion of the expandable device at least in the direction between the endplates is initiated. As the spacer member expands, the expandable device contacts the vertebral endplates to maintain the distraction provided by the impactor as the impactor is withdrawn from the disc space.

Various techniques for expanding the expandable device to maintain distraction are contemplated. For example, in one procedure a flowable material injected into the spacer member expands the spacer member and provide the expansion to move the first and second members away from one another and into contact with the vertebral endplates to re-distract the vertebrae, or to maintain distraction that is applied to the vertebrae. In another procedure, the expandable device is inserted into a disc space which is distracted with, for example, impactor 180, or in a disc space that has been previously distracted. Beads or ball-like members are placed into the spacer member through a lumen of the impactor instrument or of another delivery instrument in sufficient quantity to provide and maintain separation of the first and second members in contact with the vertebral endplates. The beads can be comprised of bio-active material or other suitable material compatible with the material injected to finally expand the spacer member and the expandable device.

It is further contemplated that the disc space can be distracted prior to placement of the expandable device into the spinal disc space. For example, before or after preparation of the interspace to receive the expandable device, an implant trial is inserted into the disc space to evaluate the appropriately sized expandable device to be inserted. The trial distracts the disc space when inserted. To maintain distraction after withdrawal of the trial, a distraction system is coupled between the pedicles or other portion of the target vertebrae. In one procedure, extenders are mounted to the pedicles and extend proximally from the pedicles to a distraction device. The distraction device is configured to maintain separation of the extenders by engaging and maintaining separation of the extenders at the proximal ends of the extenders, or by a rod element secured between the extenders adjacent their attachment location with the pedicles. The distraction device is secured to the extenders until the expandable device is implanted and expanded, and can then be removed from the patient. In another procedure, distraction of the disc space that is provided by trials or other instrumentation is maintained by placing the patient in traction until the expandable device is implanted and expanded.

Any suitable osteogenic material or composition is contemplated for injecting into or expanding the spacer members herein. Examples of suitable materials include autograft, allograft, xenograft, demineralized bone, and synthetic and natural bone graft substitutes, such as bioceramics and polymers, and osteoinductive factors. The terms osteogenic material or osteogenic composition used herein broadly include any material that promotes bone growth or healing including autograft, allograft, xenograft, bone graft substitutes and natural, synthetic and recombinant proteins, hormones and the like. Natural and synthetic graft substitutes which replace the structure or function of bone are also contemplated for the osteogenic composition. Any such graft substitute is contemplated, including for example, demineralized bone matrix, demineralized bone matrix with bone chips, PMMA and other injectable synthetic bone cements, mineral compositions, and bioceramics. A vast array of bioceramic materials, including BIOGLASS®, hydroxyapatite, and calcium phosphate compositions known in the art which can be used to advantage for this purpose. Calcium compositions include bioactive glasses, tricalcium phosphates, and hydroxyapatites. Also contemplated is a graft substitute that is a biphasic calcium phosphate ceramic including tricalcium phosphate and hydroxyapatite.

In some embodiments, the osteogenic compositions are used that comprise a therapeutically effective amount to stimulate or induce bone growth of a bone inductive or growth factor or protein in a pharmaceutically acceptable carrier. Osteoinductive factors that are recombinant human bone morphogenetic proteins (rhBMPs) are contemplated because they are readily available and do not contribute to the spread of infectious diseases. The bone morphogenetic protein can be a rhBMP-2, rhBMP-4 or heterodimers thereof. However, any bone morphogenetic protein is contemplated including bone morphogenetic proteins designated as BMP-1 through BPM-13. The choice of carrier material for the osteogenic composition is based on biocompatibility, biodegradability, mechanical properties, and interface properties as well as the structure of the expandable device. Potential carriers include calcium sulphates, polylactic acids, polyanhydrides, collagen, calcium phosphates, polymeric acrylic esters, and demineralized bone. The carrier may be any suitable carrier capable of delivering proteins. The carrier can be capable of being eventually resorbed into the body, such as an absorbable collagen sponge. Another carrier is biphasic calcium phosphate ceramic in the form of blocks. The osteoinductive factor can be introduced into the carrier in any suitable manner. For example, the carrier may be soaked in a solution containing the factor.

Figure 15A:
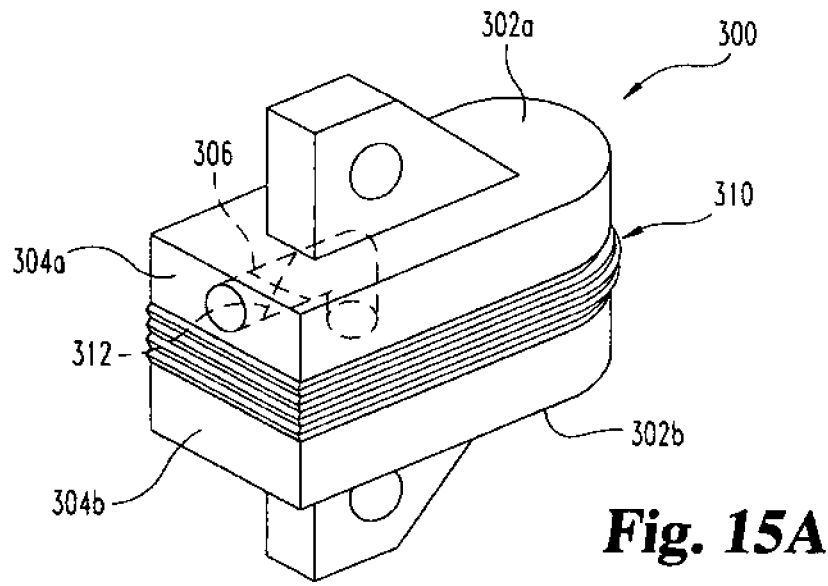
FIGS. 15A and 15B show various means for connecting an expansion instrument with expandable devices.
Figure 15B:
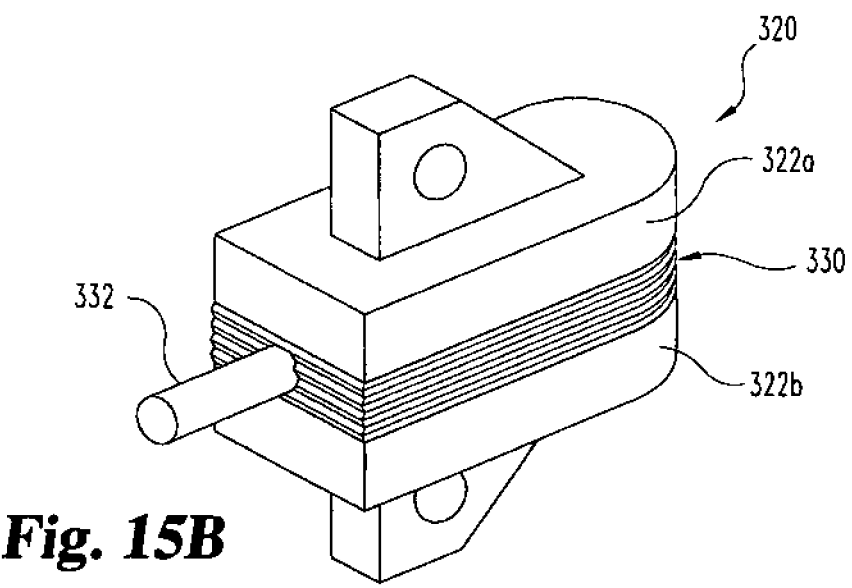

FIGS. 15A and 15B show various port arrangements for delivery of material into any of the spacer member embodiments discussed herein. In FIG. 15A, expandable device 300 is shown that includes any configuration of the expandable device embodiments discussed herein. Expandable device 300 includes a first member 302a and a second member 302b with expandable spacer member 310 therebetween. One of the first and second members 302a, 302b, such as first member 302a as shown, includes a port 306 extending therethrough that is in fluid communication with the interior of spacer member 310. Port 306 opens at a trailing end wall 304a of first member 302a for access when expandable device 300 is implanted. An injection instrument, such as instrument 200 discussed above, is coupled to port 306 to deliver material to spacer member 310 to expand it. Trailing end wall 304b of second member 302b may similarly be provided with a port if desired. Providing the port in one or both of the first and second members 302a, 302b eliminates any defect or opening in the spacer member 310, enhancing the ability of spacer member 310 to contain the material even if the material was injected into the spacer member under pressure.

In one embodiment, port 306 includes a valve structure 312 to prevent the material from back-flowing and/or the expelling of material from the interior of spacer member 310 through port 306. Valve structure 312 may be in the form of a flap, gasket or other check valve structure that allows material to pass therethrough into spacer member 310 but not out of spacer member 310. The valve structure 312 opens in response to material flow or pressure, or is manually opened and closed through an actuator means provided on the expandable device or provided by the action of the material delivery instrument on the valve structure.

In FIG. 15B, another embodiment expandable device 320 is shown that is configured like any of the expandable devices discussed herein. Expandable device 320 includes another port arrangement with a port 332 that extends from and forms a part of spacer member 330. Port 332 may be provided in lieu of or in addition to ports in one of the first and second members 322a, 322b.

Figure 16A:
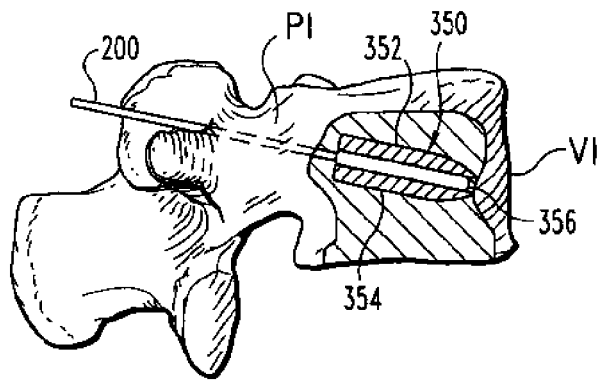
FIGS. 16A and 16B show a collapsed and expanded expandable device, respectively, positioned in a vertebral body.
Figure 16B:
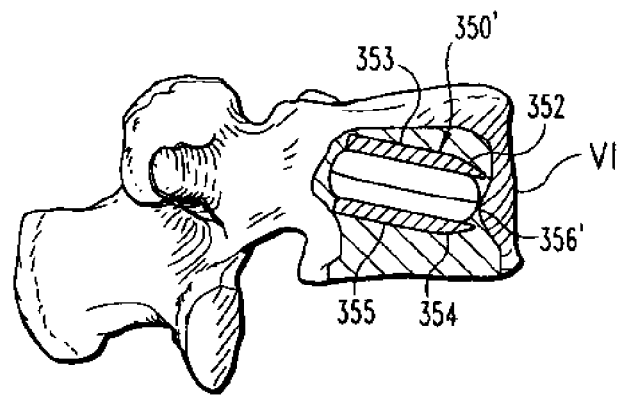

In yet other procedures, the expandable device is employed at locations other than the spinal disc space. For example, in one procedure shown in FIG. 16A, the expandable device 350 is positioned within a vertebral body V1 in a collapsed or unexpanded condition. Expandable device 350 can include first and second rigid members 352, 354 and an enlargeable spacer member 356 therebetween. Expandable device 350 can include a configuration with any one or combination of features disclosed for the expandable devices herein. Expandable device 350 can be positioned through a pedicle P1 of vertebral body V1 in a posterior approach, or through a lateral or anterior approach to the vertebral body. In one embodiment, first and second members 352, 354 can include threads 353, 355, respectively, extending therealong that facilitate insertion through bony tissue and into the vertebral body V1. Material delivery instrument 200 is engaged to expandable device 350 through the approach to vertebral body V1. Material is delivered to spacer member 356 through delivery instrument 200 to expand spacer member 356 as shown by spacer member 356' in FIG. 16B, compressing the cancellous bone in vertebral body V1 and restoring the height and/or shape of vertebral body V1 to treat, for example, a compression fracture.

In one embodiment, spacer member 356 is configured to expand primarily uni-directionally and orthogonally to first and second members 352, 354 to increase the space between first and second members 352, 354 and restore the vertebral body height between endplates while compressing cancellous bony tissue. Other embodiments contemplate that spacer member 356 also expands outwardly from first and second members 352, 354 to emerge from the space between first and second members 352, 254 and compress cancellous bony tissue to restor the overall shape of the vertebral body.

Figure 17A:
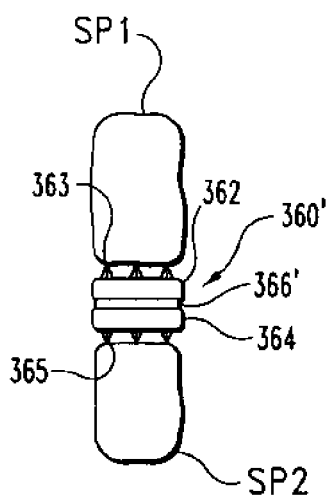
FIGS. 17A and 17B show a collapsed and expanded expandable device, respectively, positioned between spinous processes.
Figure 17B:
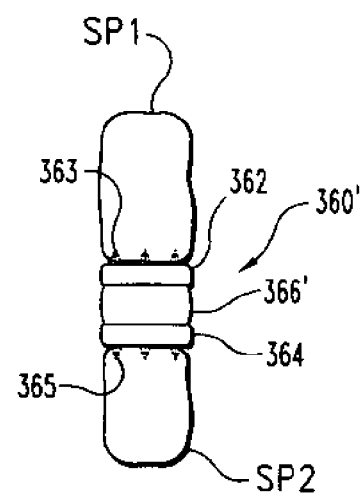

In yet another procedure shown in FIG. 17A, the expandable device 360 is positioned between spinous processes SP1 and SP2 of adjacent vertebrae with the expandable device 360 in a collapsed or unexpanded condition. Expandable device 360 can include first and second rigid members 362, 364 and an enlargeable spacer member 366 therebetween. Expandable device 360 can include a configuration with any one or combination of features disclosed for the expandable devices herein. In one embodiment, first and second members 362, 364 can include spikes or teeth 363, 365, respectively, extending therefrom and spaced therealong that engage the bony tissue in contact therewith. The tapered leading insertion end 361 of expandable device 360 can guide and facilitate placement between the spinous processes SP1, SP2. Material is delivered to spacer member 366 to expand spacer member 366 as shown by spacer member 366' in FIG. 17B, distracting and separating the spinous processes to treat, for example, spinal stenosis.

Figure 18A:
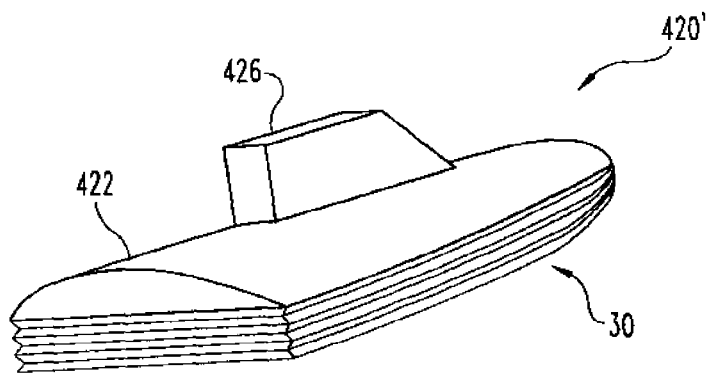
FIGS. 18A and 18B shown another embodiment collapsed and expanded expandable device, respectively.
Figure 18B:
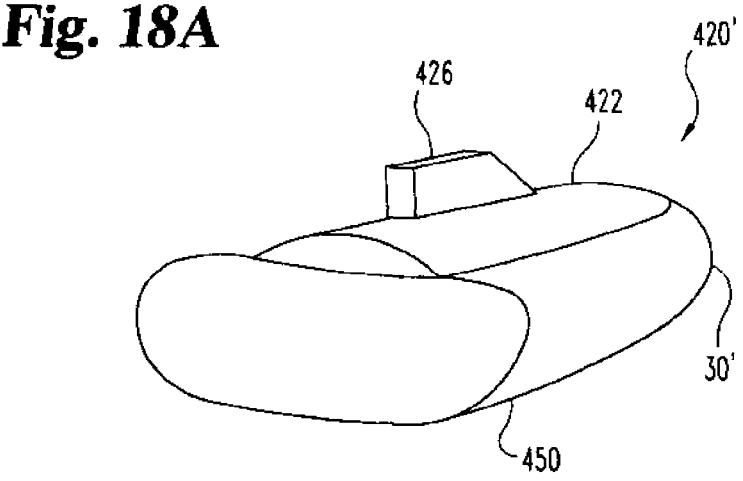
Figure 18C:
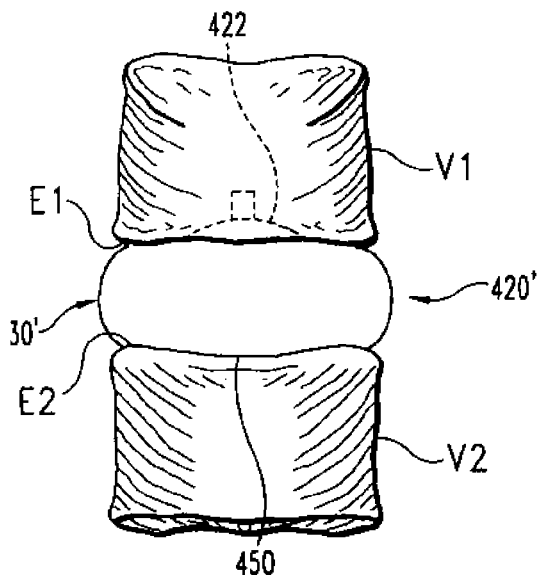
FIG. 18C shows the expanded expandable device of FIG. 18B between adjacent vertebrae.

FIGS. 18A and 18B show another embodiment of expandable device 420 designated as 420'. Expandable device 420' includes spacer member 30 in the collapsed configuration in FIG. 18A, and is shown in the enlarged or expanded configuration in FIG. 18B as spacer member 30'. Expandable device 420' differs from expandable device 420, however, in that it includes a single rigid member 422 on one side only of spacer member 30. Rigid member 422 includes at least one engagement member 426, and is configured like one of the first and second members 422*a*, 422*b* discussed above. In the collapsed configuration, spacer member 30 is confined substantially or entirely within the footprint defined by the adjacent inner surface of rigid member 422. The opposite side of spacer member 30 forms a vertebral engaging surface 450 that is positioned directly in contact with the respective adjacent vertebra or bone when expanded, as shown in FIG. 18C. Rigid end member 422 is positioned in contact with vertebra V1 to anchor device 420' to vertebra V1. Providing a single rigid member 422 facilitates insertion of device 420' into the disc space while further decreasing the overall height of the expandable device 420' when in the collapsed configuration since a rigid member is not provided on the other side of spacer member 30.

It is contemplated that expandable device 420' could be rotated so that member 422 engages vertebra V2 and contact surface 450 of spacer member 30' contacts the endplate of vertebra V1. It is also contemplated that expandable device is employed intravertebrally, or is employed between spinous processes. It is further contemplated that spacer member 30 can be provided with a shape and configuration of any of the spacer member embodiments discussed herein, and that rigid member 422 can be provided in a shape and configuration of any of the rigid member embodiments discussed herein. Expandable device 420' can also be configured for and positioned into the disc space from any approach to the disc space as discussed herein.

Various shapes and expansion characteristics for the expandable devices are contemplated as discussed herein. When viewed from above or below in the axial plane of the spinal column, the expanded device may be provided with an outer footprint formed and defined by the spacer member that is circular, oval, kidney, concave-convex, rectangular, or polygonal in shape. The first and second members positioned on the upper and lower sides of the expanded spacer member can have a different shape than the expanded spacer member. For example, the upper and lower members can have a rectangularly shaped footprint superimposed or located on the circular or oval shape of the expanded spacer. This unexpanded footprint is defined by the perimeters of the first and second member in which the spacer member is initially confined or located before expansion. The perimeters of the first and second members maintain this shape in the axial plane after expansion of the spacer member. The upper and lower members engage the adjacent vertebrae within the perimeters defined thereby. The differing shapes between the spacer member and the first and second members provide for first and second members that securely engage the vertebrae and a spacer member that provides balanced support of the spinal column loads while permitting insertion through a minimally invasive access portal, such as a sleeve, cannula, retractor, micro-incision or other portal. Other footprints or outer perimeter shapes defined by the first and second members are contemplated, including circular, oval, and polygonal shapes. Irregular shapes are also contemplated, as well as rounded and/or tapered ends or portions that provide a reduced width and/or height of one or both of the first and second members toward the leading insertion ends thereof to facilitate insertion into the disc space and/or restoration of angulation between the vertebral endplates to be supported.

Although only a few exemplary embodiments of this invention have been described in detail above, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. Accordingly, all such modifications are intended to be included within the scope of this invention.

What is claimed is:

1. A spinal stabilization device, comprising:
   a first member including a body extending along a longitudinal axis between a leading end and a trailing end, said body further including an outer surface and an opposite inner surface extending between said leading and trailing ends, said body further including a side connecting said outer and inner surfaces that defines a first perimeter;
   a second member including a body extending along the longitudinal axis between a leading end and a trailing end, said body further including an outer surface and an opposite inner surface extending between said leading and trailing ends, said body further including a side connecting said outer and inner surfaces that defines a second perimeter; and
   a spacer member extending between said first and second members, said spacer member including a collapsed configuration wherein said spacer member is substantially located within at least one of said first and second perimeters of said first and second members and an expanded configuration wherein said spacer member includes a first portion that expands outwardly from said first and second perimeters in a first direction and a second portion that expands outwardly from said first and second perimeters in a second direction opposite the first direction,
   wherein at least one of said first and second members includes a keel projecting from said outer surface along said axis configured for disposal in a channel formed in tissue, the keel including a first end defining a first portion having a uniform height and a second portion that is tapered between the first portion and a second end of the keel.

2. A spinal stabilization device, comprising:
   a first member including a rigid body extending along a longitudinal axis;
   a second member including a rigid body extending along the longitudinal axis; and
   a spacer member extending between said first and second members, said spacer member being collapsed for implanting in a spinal disc space of a spinal column wherein said spacer member and said first and second members together define a first shape in an insertion configuration when viewed in an axial plane of the spinal column and said spacer member is expandable to an expanded configuration wherein said spacer member defines a second shape when viewed in the axial plane that extends outwardly from said first and second members and said first and second members retain said first shape, wherein said first and second members each include a keel projecting from an outer surface thereof extending parallel to said axis configured for disposal of a channel formed in tissue, the keel including a first end defining a first portion having a uniform height and a second portion that is tapered between the first portion and a second end of the keel.

3. The device of claim 2, wherein said first shape is rectangular and said second shape is oval.

4. The device of claim 2, wherein said first shape is rectangular and said second shape is circular.

5. The device of claim 2, wherein said spacer member expands eccentrically from said first and second members.

6. The device of claim 2, wherein said spacer member defines at least one chamber and material is injected into said chamber to form said second shape.

7. The device of claim 2, wherein said spacer member includes a side extending between said first and second members and in said collapsed configuration said side is folded onto itself.

8. The device of claim 2, wherein said first and second members each include at least one engagement member extending therefrom in opposite directions from one another for engaging an adjacent vertebral body.

9. The device of claim 2, wherein said first and second members each include:
   a flat, plate-like body extending between a leading end and a trailing end, said body further including an outer surface and an opposite inner surface, said body further including a pair of opposite sides connecting said outer and inner surfaces and extending between said leading and trailing ends.

10. A method for stabilizing a spinal disc space between adjacent vertebrae of a spinal column, comprising:
   accessing the spinal disc space from an approach to the spinal column;
   forming a channel in an endplate of a first vertebra and a channel in an endplate of a second adjacent vertebra;
   positioning an expandable device in the spinal disc space along the approach, said device comprising upper and lower members each including a body extending along a longitudinal axis between a leading end and a trailing end, the body including a keel projecting from an outer surface thereof along the axis, the keel including a first end defining a first portion having a uniform height and a second portion that is tapered between the first portion and a second end of the keel, wherein the device has an insertion configuration defining a first footprint in the spinal disc space when viewed in an axial plane of the spinal column; and
   expanding a spacer member of the expandable device to move the upper and lower members of the expandable device away from one another in the spinal disc space and transversely to the approach so that the keels are disposed in the channels and the expanded spacer member extends outward from the first footprint and substantially occupies the spinal disc space and the upper and lower members engage the adjacent vertebrae while maintaining the first footprint.

11. A spinal stabilization device, comprising:
   a spacer member that is manipulatable between a collapsed configuration and an enlarged, expanded configuration, wherein said spacer member includes a first side and an opposite second side; and
   a single rigid member including a body extending along a longitudinal axis between a leading end and a trailing end, said body further including an outer surface and an opposite inner surface extending between said leading and trailing ends, wherein said rigid member is secured to said first side of said spacer member along said inner surface, and in said collapsed configuration of said spacer member said spacer member resides primarily within a footprint of said rigid member along said inner surface and in said enlarged configuration said spacer member expands outwardly from said inner surface of said rigid member,
   wherein said rigid member includes a keel projecting from said outer surface along said axis configured for disposal in a channel formed in tissue, the keel including a first end defining a first portion having a uniform height and a second portion that is tapered between the first portion and a second end of the keel.

12. The device of claim 11, wherein said keel extends outwardly from said outer surface in a direction opposite said inner surface.

13. A spinal stabilization device, comprising:
   a first member including a body extending along a longitudinal axis between a leading end and a trailing end, said body further including an outer surface and an opposite inner surface extending between said leading and trailing ends, said body further including a side connecting said outer and inner surfaces that defines a first perimeter;
   a second member including a body extending along the longitudinal axis between a leading end and a trailing end, said body further including an outer surface and an opposite inner surface extending between said leading and trailing ends, said body further including a side connecting said outer and inner surfaces that defines a second perimeter; and
   a spacer member extending between said first and second members, said spacer member including a collapsed configuration wherein said spacer member is substantially located within at least one of said first and second perimeters of said first and second members and an expanded configuration wherein said spacer member includes a first portion that expands outwardly from said first and second perimeters in a first direction and a second portion that expands outwardly from said first and second perimeters in a second direction opposite the first direction.

14. A spinal stabilization device, comprising:
   a spacer member that is manipulatable between a collapsed configuration and an enlarged, expanded configuration, wherein said spacer member includes a first side and an opposite second side; and
   a single rigid member including a body extending along a longitudinal axis between a leading end and a trailing end, said body further including an outer surface and an opposite inner surface extending between said leading and trailing ends, wherein said rigid member is secured to said first side of said spacer member along said inner surface, and in said collapsed configuration of said spacer member said spacer member resides primarily within a footprint of said rigid member along said inner surface and in said enlarged configuration said spacer member expands outwardly from said inner surface of said rigid member.

\* \* \* \* \*